(12) United States Patent
Kemp et al.

(10) Patent No.: US 8,017,921 B2
(45) Date of Patent: Sep. 13, 2011

(54) APPARATUS FOR IRRADIATION OF FLUID WITH ELECTROMAGNETIC RADIATION AND METHOD FOR THE SAME

(75) Inventors: Douglas Kemp, St. John's (CA); Leonie Rosenstiel, Albuquerque, NM (US); Jeffrey Fry, St. Philip's (CA); Hugh Gibson, Mt. Pearl (CA)

(73) Assignee: Lumen Associates, Inc. (CA)

( * ) Notice: Subject to any disclaimer, the term of this patent is extended or adjusted under 35 U.S.C. 154(b) by 394 days.

(21) Appl. No.: 12/097,832

(22) PCT Filed: Dec. 11, 2006

(86) PCT No.: PCT/CA2006/002002
§ 371 (c)(1),
(2), (4) Date: Oct. 9, 2008

(87) PCT Pub. No.: WO2007/071018
PCT Pub. Date: Jun. 28, 2007

(65) Prior Publication Data
US 2009/0159813 A1     Jun. 25, 2009

(30) Foreign Application Priority Data
Dec. 19, 2005 (CA) .................................... 2530677

(51) Int. Cl.
*G01N 23/00* (2006.01)
(52) U.S. Cl. ...................... 250/455.11; 422/24; 604/6.08
(58) Field of Classification Search ............. 250/455.11, 250/436, 432 R; 422/22, 24, 186.3; 604/6.08, 604/4.01, 28, 187
See application file for complete search history.

(56) References Cited

U.S. PATENT DOCUMENTS

| 5,300,019 A | 4/1994 | Bischof et al. |
| 5,399,314 A | 3/1995 | Samuel et al. |
| 5,539,209 A | 7/1996 | Maarschalkerweerd |
| 6,245,570 B1 | 6/2001 | Grimm et al. |
| 6,696,023 B2 | 2/2004 | Grimm et al. |

(Continued)

FOREIGN PATENT DOCUMENTS

| WO | 2003063915 | 8/2003 |
| WO | 2003090795 | 11/2003 |

OTHER PUBLICATIONS

International Search Report for corresponding PCT Application No. PCT/CA2006/002002, 2007.

(Continued)

*Primary Examiner* — Kiet Nguyen
(74) *Attorney, Agent, or Firm* — McDermott Will & Emery (57) ABSTRACT

An apparatus and method for irradiation of fluid with electromagnetic radiation, and in particular to an apparatus and method for irradiation of blood or other body fluids with ultraviolet radiation is provided. The apparatus (1) comprises a housing (2) having disposed therein at least one mount (6) adapted for receiving an ultraviolet radiation source (7) and at least one holder (8) adapted for receiving a container of the fluid. The housing (2) is adapted for operability between a first position, wherein the container (9) may be placed in the holder (8) and a second position, wherein the housing (2) may form a capsule. The apparatus further comprises a control assembly for powering the ultraviolet radiation source (7). At least a portion of the inner surface of the housing (2) is capable of reflecting the ultraviolet radiation.

15 Claims, 7 Drawing Sheets

U.S. PATENT DOCUMENTS

| | | |
|---|---|---|
| 6,719,716 B2 | 4/2004 | Clark |
| 7,077,559 B2 | 7/2006 | Hlavinka et al. |
| 7,367,961 B2 * | 5/2008 | DiMauro et al. ............. 604/187 |
| 7,404,806 B2 | 7/2008 | Clark |
| 2007/0055195 A1 * | 3/2007 | Browne ...................... 604/6.08 |

OTHER PUBLICATIONS

Written Opinion for corresponding PCT Application No. PCT/CA2006/002002, 2007.

* cited by examiner

APPARATUS FOR IRRADIATION OF FLUID WITH ELECTROMAGNETIC RADIATION AND METHOD FOR THE SAME

FIELD OF THE INVENTION

The invention relates to an apparatus and method for irradiation of fluid with electromagnetic radiation, and in particular to an apparatus and method for irradiation of blood or other body fluids with ultraviolet radiation.

BACKGROUND OF THE INVENTION

Ultraviolet Blood Irradiation (UBI) therapy, a process of irradiating blood samples with ultraviolet radiation to treat infections, was developed in the early part of the twentieth century. Irradiation of blood with ultraviolet radiation was shown to be effective in curing bacterial and viral infections, as well as wounds, asthma, and arthritis. This treatment has been shown to improve several biochemical and heamatological markers, without any significant reported toxicity or side effects.

Edblom and Knott disclosed a means for treating bloodstream infections using ultraviolet irradiation in U.S. Pat. No. 1,683,877 issued as early as 1928. Although UBI was gaining increased use into the mid-twentieth century, the emergence of chemical antibiotics saw the process drop into disuse.

However, several patents issued over the last decade or so, such as U.S. Pat. No. 5,433,738 (Stinson); U.S. Pat. Nos. 5,770,147 and 5,782,872 (Muller); U.S. Pat. Nos. 6,245,570 and 6,696,023 (Grimm et al.); U.S. Pat. No. 6,312,593 (Petrie); and U.S. Pat. No. 6,719,716 (Clark) point to a rebirth of interest in and use of UBI as a curative and possibly preventative therapy. Factors contributing to this revival of interest may be attributed, among others, to the non-pathogen specific nature of UBI treatment, emergence of antibiotic resistant strains of bacteria and viruses, and to the general public showing an increased interest in alternative forms of medical treatment.

Common features of devices used for UBI treatment include lamps that produce light in the ultraviolet region of the electromagnetic spectrum, reflectors to reflect the light onto the sample container, and power and control systems. The containers for the sample are made from materials transparent to ultraviolet radiation such as quartz or suitable polymeric materials.

The devices may be classified into two categories, viz., flow-through devices and static devices. In a typical flow-through device, exemplified in U.S. Pat. No. 6,719,716, blood drawn directly from the body of a user passes via a conduit system through a container, such as a quartz cuvette, where the blood is irradiated with ultraviolet light. The irradiated blood is then collected in a suitable collection means and returned to the user through the container, where it may be irradiated again. On the other hand, in a typical static device, blood is withdrawn from the user using a standard syringe, transferred to a cuvette for irradiation, and returned to the user after irradiation by means of another syringe. An example of a device of the aforementioned type is disclosed in U.S. Pat. No. 5,770,147.

The devices and methods of prior art have inherent disadvantages. For example, flow-through devices involve the use of elaborate plastic tubing, bags, separate cuvettes, and other paraphernalia. This complexity increases, inter alia, the possibility of the blood being contaminated from external sources and an increase in the risk of health hazards to the user. Static devices involve the transfer of blood from the container in which it is drawn from the user to a container where it is irradiated and to a different container in which it is returned to the user. This multi-step transfer process also increases the risk of contamination. The use of several components in a single treatment also increases the overall cost of UBI therapy.

SUMMARY OF THE INVENTION

To overcome the above-mentioned problems, it is, therefore, an object of the present invention to provide an improved apparatus and method for irradiation of fluid with electromagnetic radiation, and in particular to provide an improved apparatus and method for irradiation of blood or other body fluids with ultraviolet radiation.

A further object of this invention is to provide a compact, portable, and inexpensive apparatus for the irradiation of fluid with ultraviolet radiation that eliminates contamination of the fluid.

According to an aspect of the invention, there is provided an apparatus for irradiation of a fluid by ultraviolet radiation. The apparatus comprises a housing having disposed therein at least one mount adapted for receiving an ultraviolet radiation source and at least one holder adapted for receiving a container of the fluid. The housing is adapted for operability between a first position, wherein the container may be placed in the holder and a second position, wherein the housing may form a capsule. The apparatus further comprises a control assembly for powering the ultraviolet radiation source. At least a portion of the inner surface of the housing is capable of reflecting the ultraviolet radiation.

In an embodiment of the present invention, the housing may comprise a pair of housing portions hingedly connected to allow movement of the portions between the first and second positions. The control assembly may be provided outside the housing.

In another embodiment of the present invention, a base assembly adapted for mounting the housing and/or the control assembly may be provided. The base assembly may further comprise a support having a pivot and a mounting surface for mounting the housing. The support may be adapted to oscillate the housing. The base assembly may also comprise at least one mechanical means to oscillate the housing. The mechanical means may be a motor with gear and cam mechanism. The mechanical means may be adapted to displace the housing in a periodic circular motion.

In yet another embodiment of the present invention, the control assembly may comprise ballasts for the ultraviolet radiation sources. The control assembly may further comprise actuating means for controlling the mechanical means. The control assembly may also comprise at least one timing-control means for controlling the ultraviolet radiation source and/or the mechanical means. The control assembly may further comprise shut-off means for preventing the operation of the ultraviolet radiation source and/or mechanical means when the housing is in the first position.

In a further embodiment of the present invention, the control assembly may comprise a microprocessor to facilitate data entry, storage and retrieval, and output.

In an embodiment of the present invention, a sensor may be provided to monitor the output of the ultraviolet radiation source. Temperature-regulating means maintaining the environment enclosed by the housing within a pre-determined temperature range may also be provided. The temperature-regulating means may comprise ventilation ducts, a cooling element and/or a heating element.

In yet another embodiment of the present invention, at least a portion of the inner surface of the housing may be made of or coated with a reflective material. The reflective material may be aluminum or silver. The inner surface of the housing may have a faceted-elliptical cross-section.

In an embodiment of the present invention, the mount may comprise a focusing lens to focus the ultraviolet radiation onto the container.

In another embodiment of the present invention, the container and/or the holding means may be made of an ultraviolet radiation-permeable material, such as quartz, or a polymeric material. The ultraviolet radiation source may be an ultraviolet lamp.

In yet another embodiment of the present invention, the container may be a syringe. The holder may be a tray designed for slidable access when the housing is in the first position.

According to another aspect of the present invention, there is provided a syringe barrel having a proximal end for receiving a plunger rod assembly; a hollow central body portion capable of holding fluids; and a distal end having a passage for receiving and dispensing the fluids from the hollow central body portion, wherein the central body portion is of a rounded-rectangular or a racetrack-shaped cross-section and a chamber is disposed on the distal end of the syringe barrel in the vicinity of the passage and is in fluid communication with the central body portion and the passage.

In an embodiment of the present invention, there is provided a plunger rod assembly for use in the syringe barrel. The plunger rod assembly may comprise a plunger head portion and a plunger rod portion, and the plunger rod portion may be removably attached to the plunger head portion.

According to another aspect of the present invention, there is provided a syringe comprising a syringe barrel and a plunger rod assembly, wherein the syringe barrel has a proximal end for receiving the plunger rod assembly; a hollow central body portion capable of holding fluids; and a distal end having a passage for receiving and dispensing the fluids from the hollow central body portion, wherein the central body portion is of a rounded-rectangular or a racetrack-shaped cross-section and a chamber is disposed on the distal end of the syringe barrel in the vicinity of the passage and is in fluid communication with the central body portion and the passage; and the plunger rod assembly comprises a plunger head portion and a plunger stem portion, wherein the plunger stem portion is removably attached to the plunger head portion.

In another embodiment of the invention, the syringe further comprises at least one weighted object contained within the barrel. The weighted objects may be capable of moving freely within the confines of the barrel. The weighted objects may be dimensioned to be accommodated in the chamber of the barrel and may also be dimensioned to be larger than the passage at the distal end of the barrel. The weighted objects may be spherical in shape and may be made of an inert material.

According to a further aspect of the present invention, there is provided a method for irradiation of blood with ultraviolet radiation comprising the steps of withdrawing a pre-determined amount of blood from a user using the syringe comprising a syringe barrel and a plunger rod assembly, wherein the syringe barrel has a proximal end for receiving the plunger rod assembly; a hollow central body portion capable of holding fluids; and a distal end having a passage for receiving and dispensing the fluids from the hollow central body portion, wherein the central body portion is of a rounded-rectangular or a racetrack-shaped cross-section and a chamber is disposed on the distal end of the syringe barrel in the vicinity of the passage and is in fluid communication with the central body portion and the passage; and the plunger rod assembly comprises a plunger head portion and a plunger stem portion, wherein the plunger stem portion is removably attached to the plunger head portion; removing a first needle of the syringe and fitting a cap in place of the first needle on the syringe; removing the plunger stem from the plunger rod assembly leaving the plunger head portion in the syringe barrel; placing the syringe in a housing of an irradiation apparatus; energizing the irradiation source in order to irradiate the blood; removing the syringe from the irradiation apparatus after the completion of the irradiation; reattaching the plunger stem portion to the plunger head portion; replacing the cap with a second needle; and, returning the ultraviolet treated blood to the user.

The method may further comprise the step of oscillating said housing. At least one weighted object may be included inside a barrel of the syringe. Reflectors disposed on the inner surface of said irradiation apparatus may be used to direct the ultraviolet radiation to the syringe.

According to another aspect of the present invention, there is provided a system for irradiation of a fluid by ultraviolet radiation comprising: an apparatus comprising a housing having disposed therein at least one mount adapted for receiving an ultraviolet radiation source and at least one holder adapted for receiving a container of the fluid, and the housing being adapted for operability between a first position, wherein the container can be placed in the holder and a second position, wherein the housing forms a capsule, and a control assembly for powering the ultraviolet radiation source, wherein at least a portion of the inner surface of the housing is capable of reflecting the ultraviolet radiation; and, a syringe comprising a syringe barrel and a plunger rod assembly, wherein the syringe barrel has a proximal end for receiving the plunger rod assembly; a hollow central body portion capable of holding fluids; and a distal end having a passage for receiving and dispensing the fluids from the hollow central body portion, wherein the central body portion is of a rounded-rectangular or a racetrack-shaped cross-section and a chamber is disposed on the distal end of the syringe barrel in the vicinity of the passage and is in fluid communication with the central body portion and the passage; and the plunger rod assembly comprises a plunger head portion and a plunger stem portion, wherein the plunger stem portion is removably attached to the plunger head portion.

BRIEF DESCRIPTION OF DRAWINGS

Embodiments of the invention will now be described, by way of example, with reference to the accompanying drawings, in which:

FIG. 7(*a*) is a top plan view and FIG. 7(*b*) is a perspective view of a plunger rod assembly comprising a plunger stem portion and a plunger head portion of the syringe according to the embodiment of FIG. 5(*a*); and, FIG. 8 is a cut-open view of a distal end of the syringe according to the embodiment of FIG. 5(*a*).

DETAILED DESCRIPTION OF THE PREFERRED EMBODIMENTS

The following description is of a preferred embodiment by way of example only and without limitation to the combination of features necessary for carrying the invention into effect.

Figure 1:
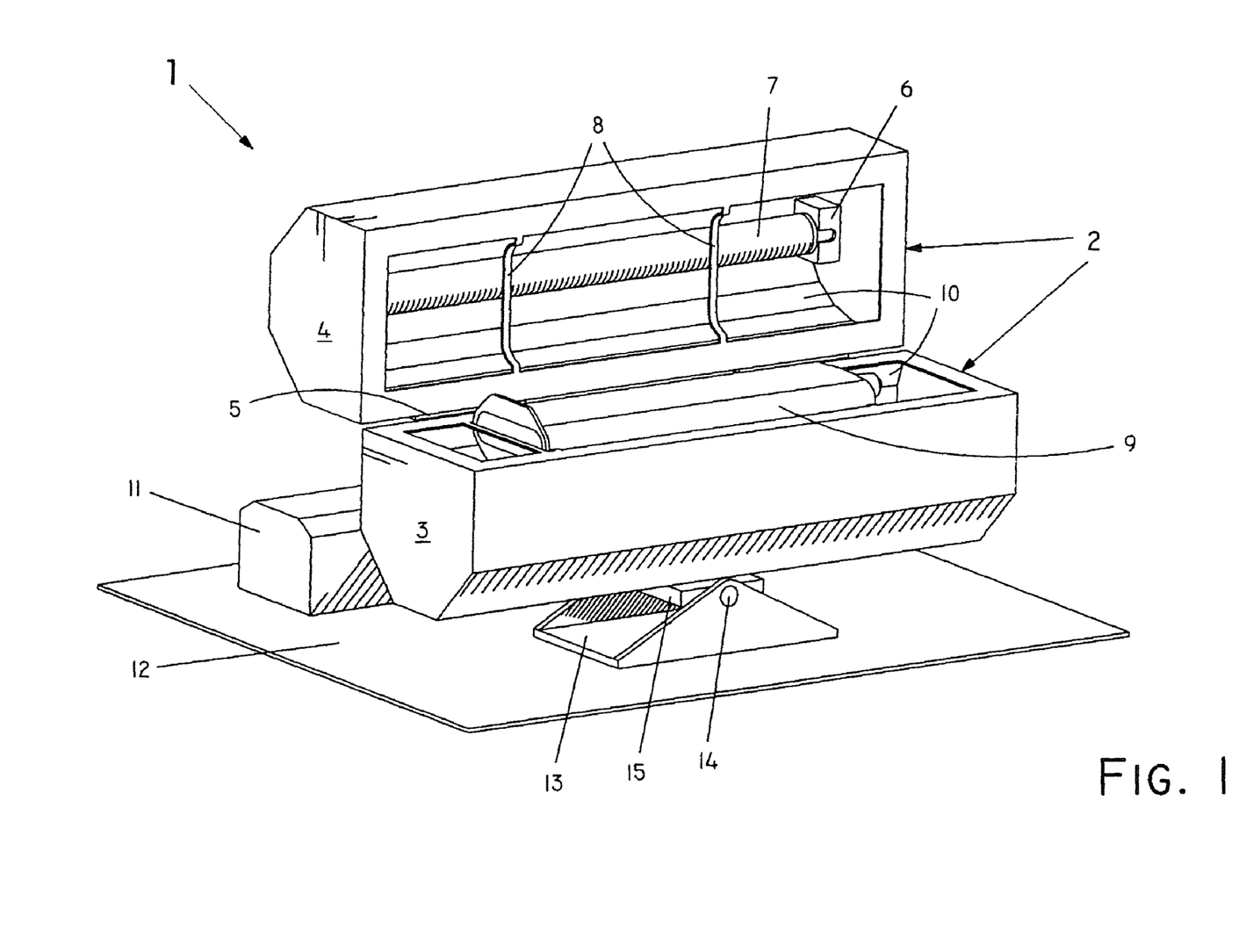
FIG. 1 is a perspective view of an apparatus for irradiation of fluid according to an embodiment of the present invention.

As shown in FIG. 1, the apparatus 1 comprises a housing 2 having a bottom housing portion 3 and a top housing portion 4 connected by means of a hinge 5 so as to facilitate the operation of the housing 2 between a first position and a second position. Mounts 6 are adapted for receiving ultraviolet radiation sources, such as ultraviolet lamps 7, and holders 8 are adapted for receiving a container 9 and are disposed in the housing 2. In the first position, the container 9 can be placed in the holders 8 and in the second position, the housing 2 forms a capsule. Reflectors 10 are disposed on a portion of the inner surface of the housing 2 and are capable of reflecting the ultraviolet radiation towards the container 9. The reflectors 10 are disposed so as to form a faceted elliptical cross-section. The faceted elliptical geometry of the reflectors 10 ensures that the radiation from the ultraviolet lamps 7 is distributed across the surface of the container 9 thereby ensuring uniform exposure of the sample contained therein. The apparatus 1 further comprises a control assembly for powering the ultraviolet lamps 7, such as a ballast 11 provided outside of the housing 2. Additionally, a base assembly 12 is provided for mounting the housing 2 and the ballast 11. The base assembly 12 includes a support 13 comprising a pivot 14 and a mounting surface 15 for mounting the housing 2. The control assembly and timer circuit to control the operation of the apparatus are not shown and may be in any arrangement suitable for such purposes.

Although the bottom housing portion 3 and a top housing portion 4 are shown to be connected by means of a hinge 5 in FIG. 1, it may be envisioned that the interior of the housing 2 may be accessible by other means, such as an access door. Alternatively, the holder 8 may be a tray designed for slidable access when the housing is in the first position.

Figure 2:
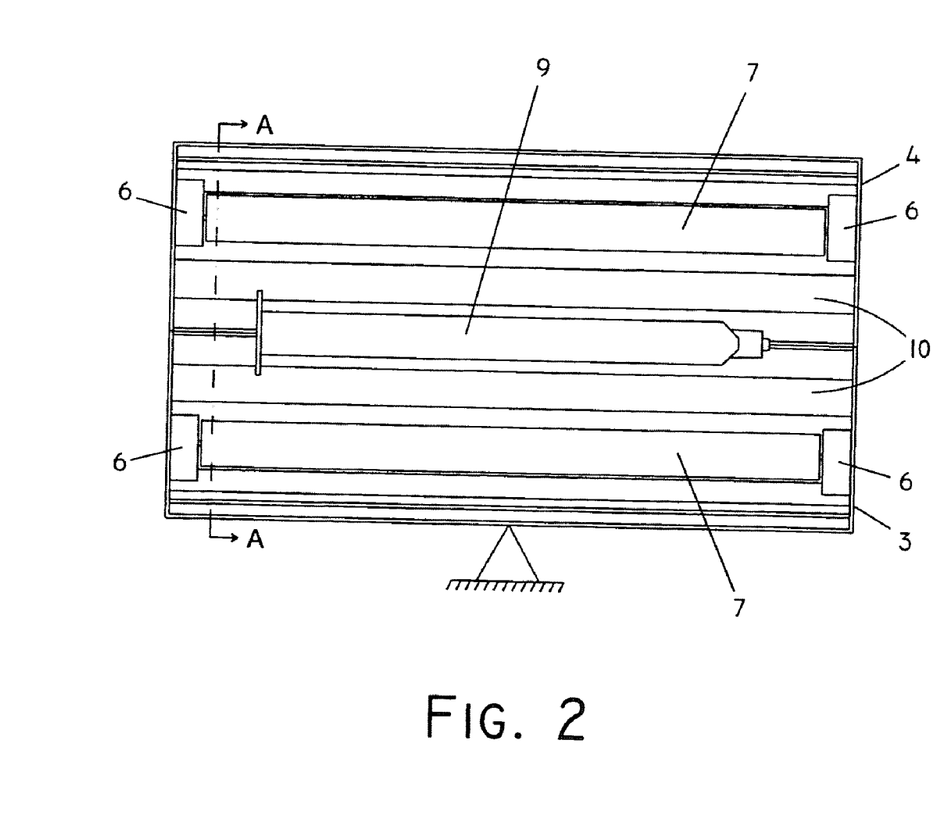
FIG. 2 is a longitudinal cross-section of the apparatus according to the embodiment of FIG. 1.
Figure 3:
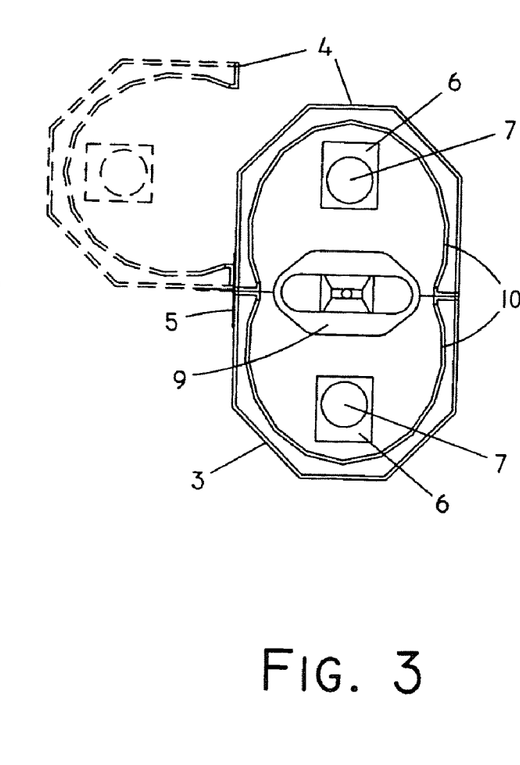
FIG. 3 is a cross-section of the apparatus according to the embodiment of FIG. 1 along the line AA of FIG. 2, a first position of the apparatus is shown in ghosted view.

FIG. 2 shows a longitudinal cross-section and FIG. 3 shows a cross-section along the line AA of FIG. 2 of the housing 2 in the second position wherein the housing 2 forms a capsule. The first position of the housing 2 wherein the interior of the housing 2 is readily accessible is shown in ghosted view in FIG. 3. As shown in FIGS. 2 and 3, two ultraviolet lamps 7 are provided, one on in each of the bottom housing portion 3 and the top housing portion 4, with the container 9 disposed therebetween. In other embodiments, a plurality of ultraviolet lamps 7 may be suitably disposed in the housing 2 so as to provide a uniform and thorough irradiation of the contents of a plurality of containers 9. One or more reflectors 10 may be disposed on the inner surface of the housing 2 to most efficiently direct the ultraviolet radiation onto the surface of the containers 9.

Figure 4:
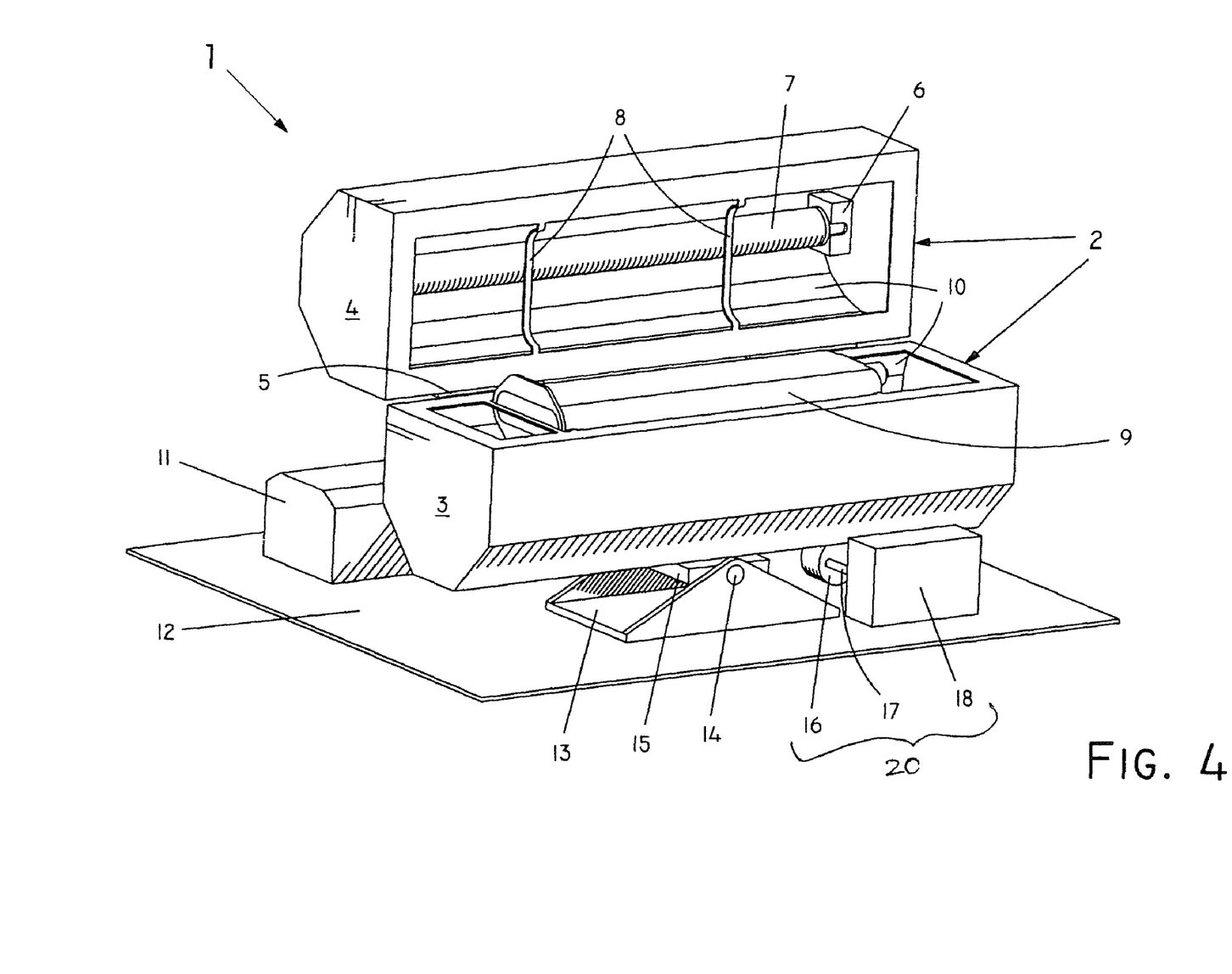
FIG. 4 is a perspective view of an apparatus for irradiation of fluid according to another embodiment of the present invention.

The support 13 of the base assembly 12 shown in FIG. 1 is provided to facilitate the oscillation of the housing 2. Oscillation of the housing 2 during the ultraviolet irradiation process causes the sample in container 9 to be uniformly exposed, thereby providing maximum benefits of the UBI treatment. As shown in FIG. 4, a mechanical means comprising a cam 16, a cam shaft 17, a motor 18, and associated gear mechanism (not shown) is provided in an alternative embodiment of the present invention. The mechanical means may be used to oscillate the housing 2 in a preferred manner so as to ensure a thorough exposure of the sample in the containers 9 to the ultraviolet radiation. Although a cam and gear mechanism is shown as an illustrative example, other mechanical means, such as a vibration table, may be envisaged for the agitation of the housing 2. One of the primary advantages of oscillating the entire housing 2, rather than oscillating the container 9 alone, is to ensure that the ultraviolet lamps 7 and the container 9 are maintained at an optimum distance and orientation relative to each other, throughout the irradiation process.

Figure 5A:
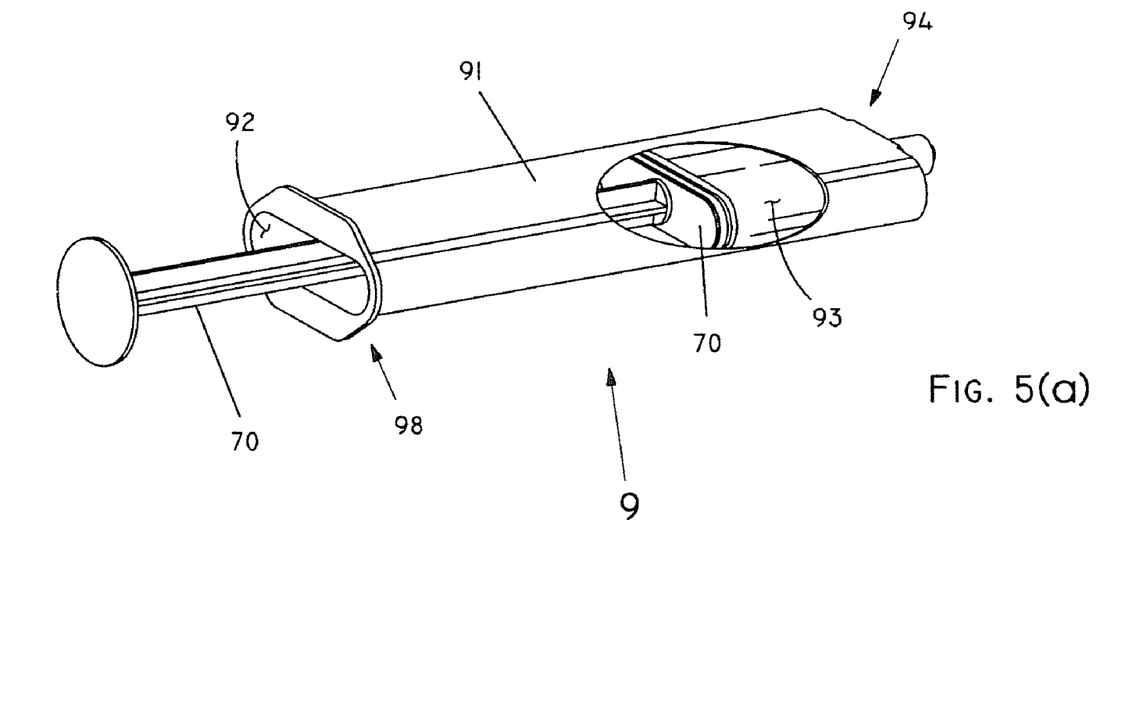
FIG. 5(a) is a perspective view of a syringe according to an embodiment of the present invention, (b) is a perspective view of the distal end of the syringe according to the embodiment of FIG. 5(a)
Figure 5B:
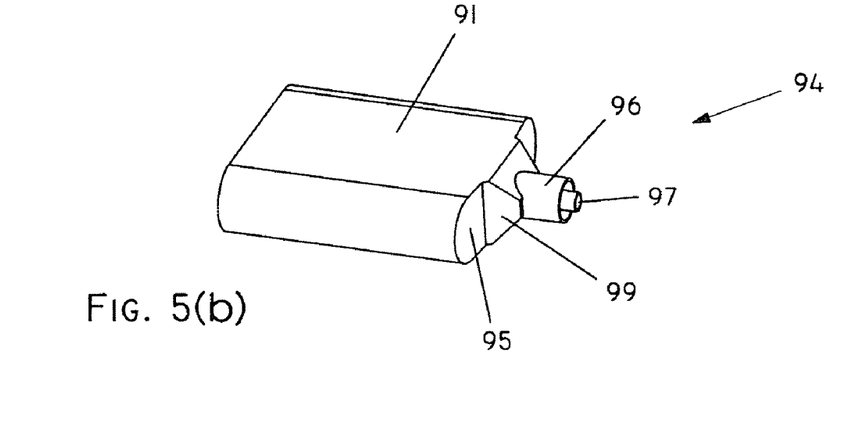
Figure 6A:
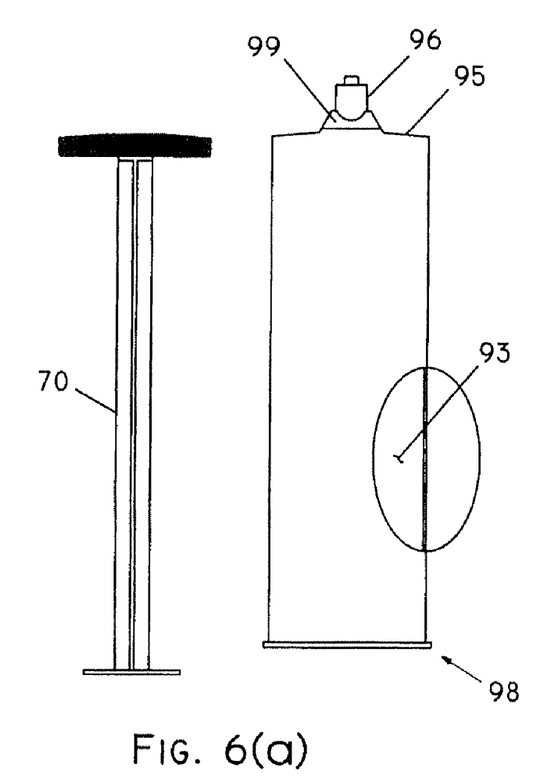
FIG. 6(a) is a top plan view of the syringe barrel and the plunger rod assembly, (b) is a side view of the syringe barrel and the plunger rod assembly, (c) is an end view of the proximal end of the syringe barrel, and (*d*) is an end view of the distal end of the syringe barrel of the syringe according to the embodiment of FIG. 5(*a*)
Figure 6B:
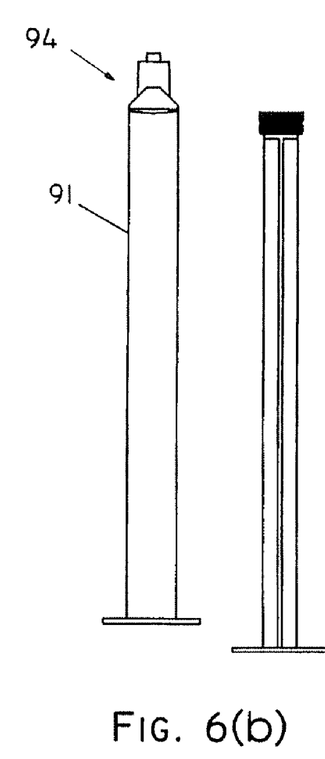
Figure 6C:
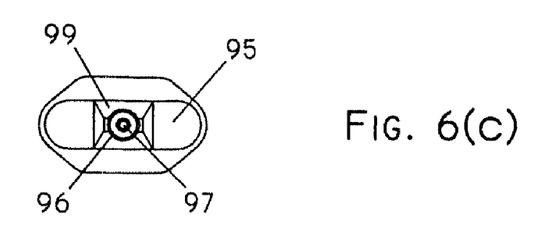
Figure 6D:
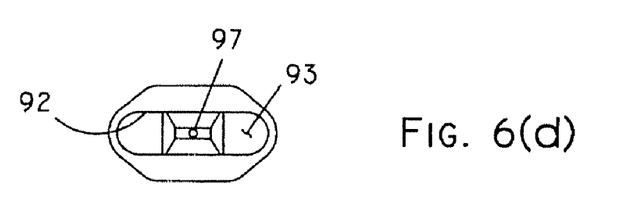

The container 9, as shown in FIGS. 5 and 6, is a custom-designed syringe made of a material transparent to ultraviolet radiation, such as quartz, ultraviolet-transparent polymer, etc. FIG. 5 shows a perspective of a syringe 9 according to an embodiment of the present invention. The syringe 9 comprises a syringe barrel 91 having an inner surface 92 defining a hollow central body portion 93, and a plunger rod assembly 70. The syringe barrel 91 comprises a distal end 94 and a proximal end 98. The distal end 94 terminates in an end wall 95 and a passage 97 for receiving and dispensing the fluids from the hollow central body potion 93. A male luer fitting 96, for attaching an injection needle or a connector equipped with a tubing conduit, is affixed on the outer side of the passage 97 as shown in FIG. 5(*b*). The proximal end 98 is dimensioned to receive the plunger rod assembly 70. As shown in FIGS. 5(*a*) and (*b*), the syringe barrel 91 is of a rounded-rectangular or a racetrack-shaped cross-section. A chamber 99 is disposed on the distal end 94 of the syringe barrel 91 in the vicinity of the passage and is in fluid communication with the hollow central body portion 93 and the passage 97.

FIGS. 6(*a*) and (*b*) show a front view and side view, respectively, of the syringe barrel 91 and the plunger rod assembly 70, FIG. 6(*c*) shows a view of the distal end 94 of the syringe 9, looking directly at the luer fitting 96 and the chamber 99, and FIG. 6(*d*) shows a view of the proximal end 98 of the syringe 9, looking down the length of the hollow central body portion 93 of the syringe 9 and showing the passage 97.

Figure 7A:
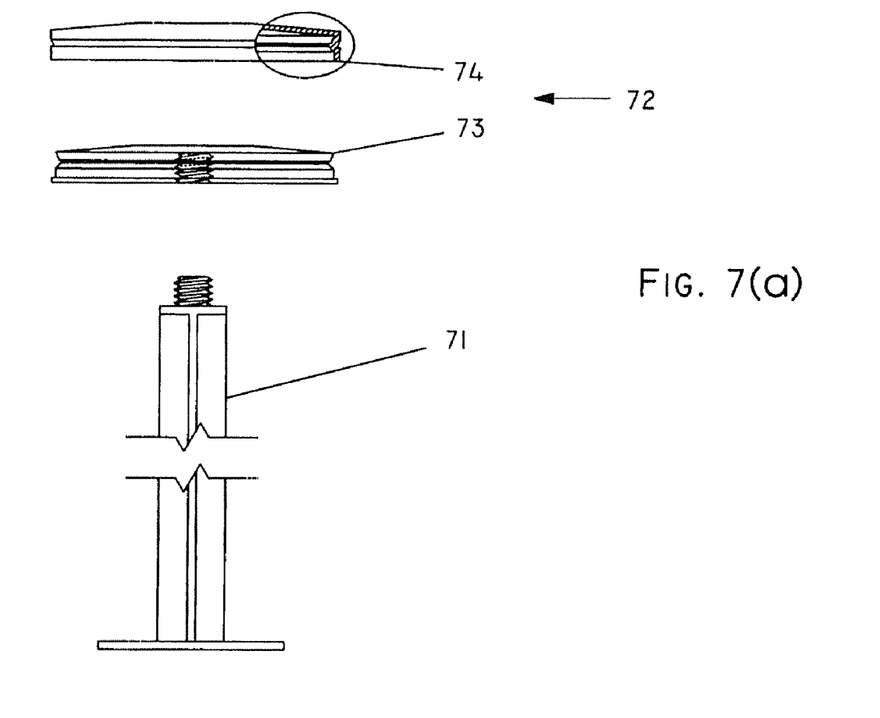
Figure 7B:
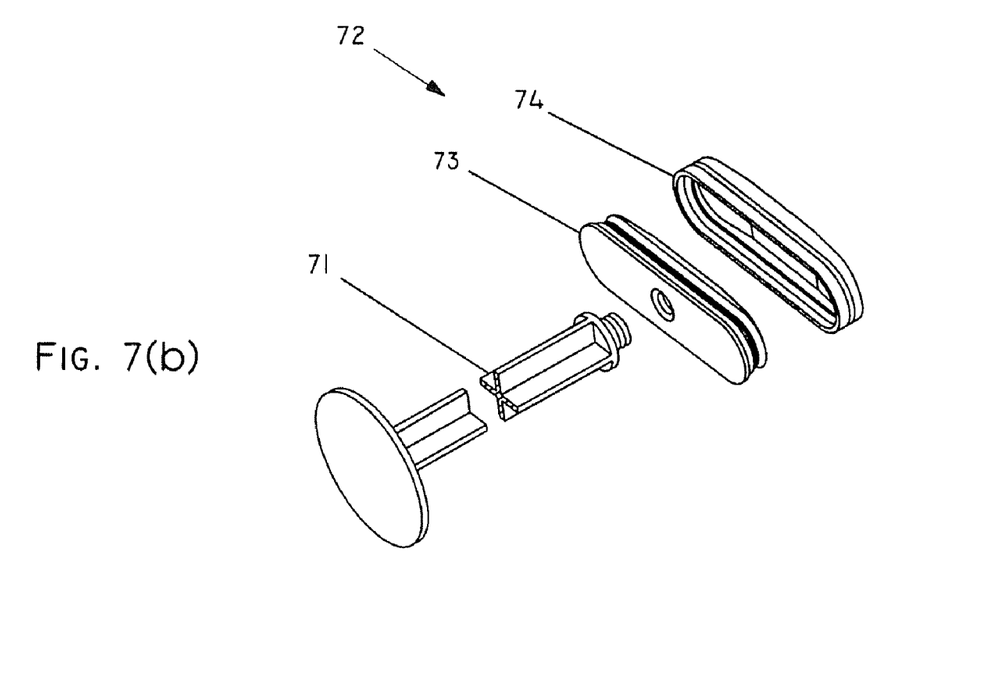

As shown in FIGS. 7(*a*) and (*b*), the plunger rod assembly 70 comprises a plunger stem portion 71, and a plunger head portion 72. The plunger head portion 72 comprises a plunger head 73, made of a solid material, and a plunger head cap 74, made of a soft polymeric material. The cap 74 is designed to fit snugly over the head 73, and to provide a tight seal against the inside surface 92 of the syringe barrel 91, thus producing a liquid-tight seal. The plunger stem portion 71 can be removably attached to the plunger head portion 72. The syringe barrel 91 and the plunger rod assembly can be used to withdraw a blood sample from a user prior to the irradiation process. Once the blood sample is withdrawn, the plunger stem portion 71 can be removed from the plunger head portion 72. The syringe 9 thus forms a container suitable for placement in the housing 2 for irradiation of the sample contained therein. Upon completion of the irradiation process, the plunger stem portion 71 can be reattached to the plunger head portion 72 to permit injection of the ultraviolet irradiated blood into the user.

The primary advantage of using a custom designed syringe as the container 9 is that it permits a blood sample to be treated in the same container by which it is withdrawn from and is returned to the user. Using the syringe as the container for the irradiation process eliminates the need for other paraphernalia such as plastic tubing, bags, cuvettes, etc. Accordingly, the need to transfer the blood sample between containers is eliminated thereby minimizing the risks of blood contamination and the exposure of blood to ambient air. Another advantage of a plunger rod assembly 70 with a removably-attached plunger stem portion 71, is that the overall length of the container 9 to be placed in the housing 2 is reduced, thus permitting the housing 2 and hence the entire apparatus 1 to be of a compact design. Also, using a custom syringe ensures that a standard syringe, on which the plunger stem is not removable, cannot be inadvertently used in the apparatus 1.

Another significant advantage in the design of the container 9 is derived from the rounded-rectangular or a racetrack-shaped cross-section of the syringe barrel 91, as shown in FIGS. 5(a) and (b). The flattened configuration maximizes the surface area exposed to the ultraviolet radiation, and additionally prevents inadvertent use of other containers, such as a standard syringe with a circular cross-section, which are made of materials that do not transmit ultraviolet radiation. Furthermore, the use of a custom syringe with a flattened configuration facilitates the use of reflectors 10 with faceted elliptical geometry. The radiation from the ultraviolet lamps 7 may then be effectively distributed uniformly across the surface of the container 9 by the reflectors 10, thus ensuring a uniform exposure of the fluid contained therein.

Figure 8A:
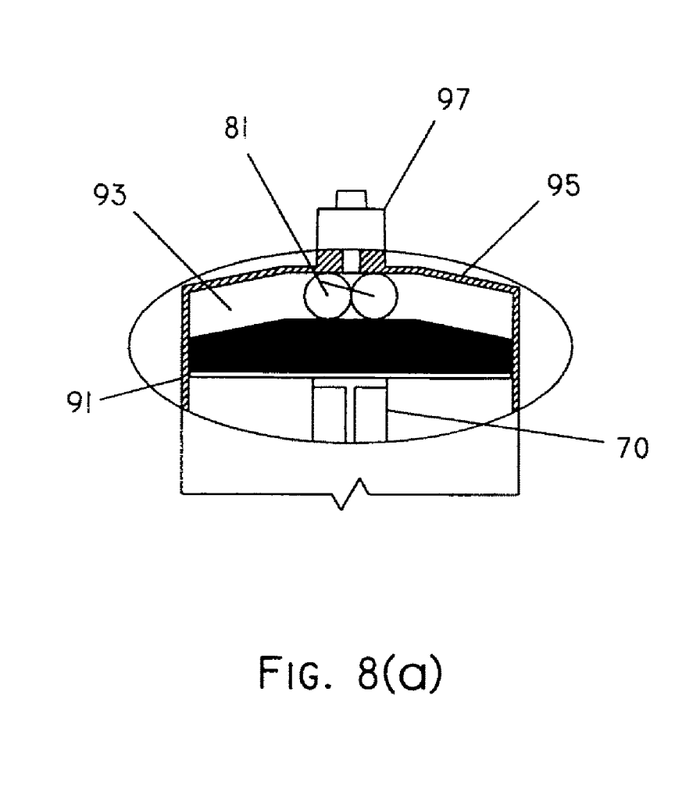
Figure 8B:
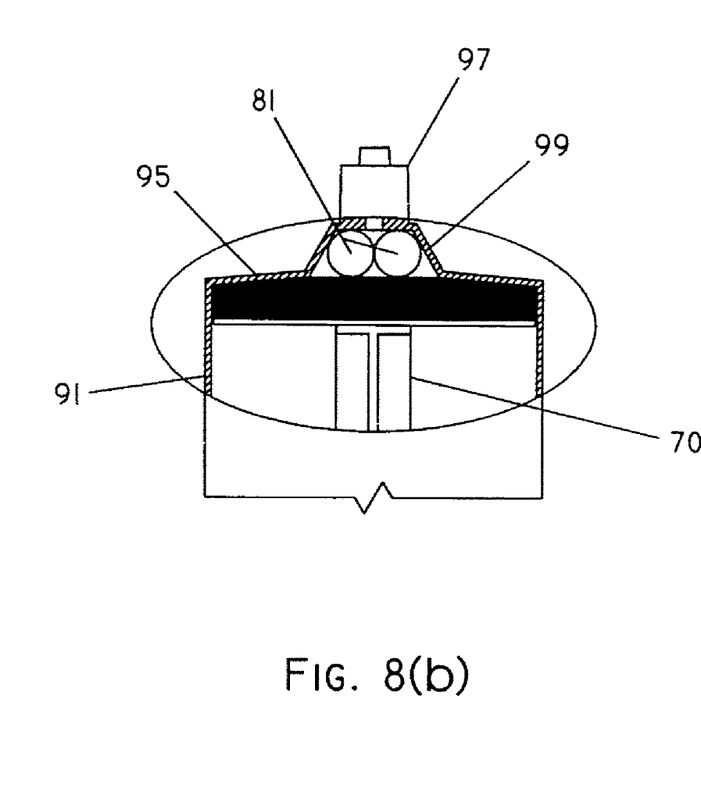

FIG. 8 is a cut-open view of the distal end 94 of the syringe 9 shown in FIG. 5(a). One or more weighted objects 81 are disposed in the hollow central body portion 93. The weighted objects 81 are made of an inert material and serve to agitate the sample contained in the container 9 during the irradiation process. For example, when the housing 2 is oscillated, either manually or mechanically during an ultraviolet irradiation process, the weighted objects 81 move between the distal end 94 and the proximal end 98 of the syringe barrel 91 and agitate the sample contained therein. The agitation helps ensure uniform exposure of the sample to the ultraviolet radiation and increases the effectiveness of the UBI treatment.

The chamber 99 disposed on the distal end 94 of the syringe barrel 91 in the vicinity of the passage 97 is dimensioned to accommodate the weighted objects 81 when the plunger rod assembly 70 is fully inserted in the syringe barrel 91 as shown in FIG. 8. The chamber 99 securely retains the weighted objects 81 during storage so that they do not rattle around inside the syringe barrel 91 and possibly cause damage to the interior of the syringe barrel 91. The chamber 99 also aids in minimizing the amount of unfilled volume inside the hollow central body portion 93 prior to drawing a blood sample, thus minimizing the amount of air with which the blood sample comes into contact.

Although the weighted objects 81 are shown to be spherical in shape in FIG. 8, they are not restricted to spheres. In fact, the weighted objects 81 may be of any suitable shape and dimension so long as they will perform the desired function of agitating the sample during the ultraviolet irradiation process.

During a typical UBI treatment session, the custom syringe 9 is fitted with an appropriate size needle (for example, 16 or 18 gauge) and using proper phlebotomy techniques, a desired amount of blood is withdrawn from a user. The needle is then removed and discarded, while a cap is fitted in its place on the syringe 9 to prevent leakage and exposure to ambient air. The plunger stem portion 71 is removed from the plunger rod portion 70 leaving the plunger head portion 72 in the syringe barrel 91. The plunger stem 71 is set aside for reuse. The syringe 9, which now serves as the container 9, is placed in the housing 2 and secured using holders 8 therein. The housing 2 is then configured to its second position and the ultraviolet lamps 7 and the mechanical means for imparting oscillation are energized. The control assembly and timer circuit are then used to control the ultraviolet irradiation and oscillation processes. After a predetermined time period of exposure; the ultraviolet lamps 7 and the mechanical means are de-energized, the housing 2 is moved to its first position and the container 9 is removed. The plunger stem portion 71 is re-attached to the plunger head portion 72, the cap is removed from the container 9, a clean needle is affixed to the container, and using proper phlebotomy techniques, the ultraviolet treated blood is returned to the user. The container/syringe 9 along with the needle assembly can be discarded thereby preventing any cross-contamination. More than one treatment session may be scheduled in order to obtain the maximum effects of UBI treatment.

The amount of blood withdrawn from a user is typically calculated based on 1 ml of blood per 1.5 lb of body weight of the user, up to a maximum of 250 ml. However, recent studies have indicated that a sample volume of 70 ml for an adult patient is sufficient for effective treatment and possibly preventative use of UBI therapy. It is understood that the sample volumes mentioned herein are for illustrative purposes only, and the actual volume needed for a particular user is best decided on a case-by-case basis.

Although in the foregoing description a preferred embodiment of the present invention has been disclosed, several other elements can be easily appended to the apparatus 1. For example, a mechanism for cooling the interior of the housing 2 during operation may be provided. A fan with associated ventilation ducts may be used to maintain the housing in a pre-determined temperature range. The control panel may include a microprocessor, sensors, and associated software to record various parameters in real time such as the total operating time, ultraviolet lamp output, intensity, wavelength, and operating temperature, etc. Safety mechanisms such as an interlock switch that prevents the operation of the apparatus 1, when the housing 2 is in its first position may also be provided.

The present invention has been described with regard to preferred embodiments. However, it will be obvious to persons skilled in the art that a number of variations and modifications can be made without departing from the scope of the invention as described herein.

INDUSTRIAL APPLICABILITY

The present invention provides an apparatus and method for irradiation of fluid with electromagnetic radiation, and in particular, an apparatus and method for irradiation of blood or other body fluids with ultraviolet radiation. Benefits derived from the use of the present invention can be enjoyed in curative and possibly preventative therapy in treating bacterial and viral infections.

What is claimed is:

1. A system for irradiation of a fluid by ultraviolet radiation comprising: an apparatus comprising a housing having disposed therein at least one mount adapted for receiving an ultraviolet radiation source and at least one holder adapted for receiving a container of said fluid, and said housing being adapted for operability between a first position, wherein said container can be placed in said holder and a second position, wherein said housing forms a capsule, and a control assembly for powering said ultraviolet radiation source, wherein at least a portion of the inner surface of said housing is capable of reflecting said ultraviolet radiation; and a syringe comprising a syringe barrel and a plunger rod assembly, wherein said syringe barrel has a proximal end for receiving said plunger rod assembly; a hollow central body portion capable of holding fluids; and a distal end having a passage for receiving and dispensing the fluids from said hollow central body portion, wherein the hollow central body portion is of a rounded-rectangular or a racetrack-shaped cross-section and a chamber is disposed on said distal end of said syringe barrel in the vicinity of said passage and is in fluid communication with the hollow central body portion and the passage; and said plunger rod assembly comprises a plunger head portion and a plunger stem portion, wherein the plunger stem portion is removably attached to the plunger head portion.

2. The use of the system according to claim 1 in irradiating a blood sample.

3. The system according to claim 1, wherein the syringe barrel, the holder or both are made of an ultraviolet permeable material.

4. The system according to claim 3, wherein the ultraviolet permeable material is quartz or a polymeric material.

5. The system according to claim 1, wherein the syringe barrel comprises at least one weighted body contained within said syringe barrel, and capable of moving freely within the confines of said syringe barrel.

6. The system according to claim 5, wherein said weighted body is dimensioned to be accommodated in said chamber of said syringe barrel and is dimensioned to be larger than the diameter of said passage.

7. The system according to claim 5, wherein said weighted body is spherical in shape.

8. The system according to claim 5, wherein said weighted body is made of an inert material.

9. The system according to claim 1, wherein the holder adapted for receiving said container of said fluid, is a tray designed for slidable access to the housing when the housing is in either said first position or said second position.

10. The system according to claim 1, wherein the inner surface of said housing has a faceted-elliptical cross-section.

11. The system according to claim 1, wherein said housing comprises a pair of housing portions hingedly connected to allow movement of said portions between said first and second positions.

12. The system according to claim 1, wherein said control assembly is provided outside of said housing.

13. The system according to claim 1, further comprising a base assembly adapted for mounting said housing, said control assembly, or both thereon.

14. The system according to claim 13 wherein said base assembly further comprises a support having a pivot and a mounting surface for mounting said housing.

15. The system according to claim 14, wherein said support is adapted to oscillate said housing.

* * * * *